United States Patent [19]

Fortney et al.

[11] Patent Number: 5,145,681
[45] Date of Patent: Sep. 8, 1992

[54] COMPOSITIONS CONTAINING PROTEASE PRODUCED BY VIBRIO AND METHOD OF USE IN DEBRIDEMENT AND WOUND HEALING

[75] Inventors: Donald Z. Fortney, Baltimore; Donald R. Durham, Gaithersburg, both of Md.

[73] Assignee: W. R. Grace & Co.-Conn., New York, N.Y.

[21] Appl. No.: 567,884

[22] Filed: Aug. 15, 1990

[51] Int. Cl.$^5$ .............................................. A61K 37/54
[52] U.S. Cl. ................................. 424/94.63; 435/220; 435/909
[58] Field of Search ...................... 424/94.63; 435/220

[56] References Cited

U.S. PATENT DOCUMENTS

| | | | |
|---|---|---|---|
| 3,409,719 | 11/1968 | Noe et al. | 424/94.67 |
| 3,677,900 | 7/1972 | Merkel | 435/220 |
| 4,276,281 | 6/1981 | Crikelair | 424/94.64 |
| 4,329,430 | 5/1982 | Klein et al. | 435/219 |
| 4,668,228 | 5/1987 | Bolton et al. | 604/307 |
| 4,865,983 | 9/1989 | Durham | 435/264 |

OTHER PUBLICATIONS

Merkel et al., "Proteolytic Activity and General Characteristics of a Marine Bacterium, Aeromonas Proteolytica SP. N.," Journal of Bacteriology (1964) 87:1227-1233.
Prytz et al., "Digestion of Human Burn Eschar by Proteolytic Enzymes," Enzymalia (1965) 28:367-376.
Boxer et al., "Debridement of Dermal Ulcers and Decubiti with Collagenese," Geriatrics (1969) 75-86.
Silverstein et al., "Laboratory Evaluation of Enzymatic Burn Wound Debridement In Vitro and In Vivo," Surgical Forum (1972) 31-33.
Falces, "Enzymes for Debridement," Western Journal of Medicine (1980) 133:59-60.
Silverstein et al., "Enzymatic and Nonsurgical Debridement," Journal of Burn Care Rehabilitation (1981) 49.
Makepeace, "Enzymatic Debridement of Burns," Burns (1982) 9:153-157.
Coopwood, "Evaluation of a Topical Enzymatic Debridement Agent," Southern Medical Journal (1976) 69:834-836.
Shakespeare et al., "The Activity of the Enzymatic Debridement Agent Travase towards a Variety of Protein Substrates," Burns (1978) 6:15-20.
Merkel et al., "Purification and Characterization of a Marine Bacterial Collagenase," Biochemistry (1978) 17:2857-2863.
Dreisbach et al., "Induction of Collagenase Production in Vibrio B-30", Journal of Bacteriology (1978) 135:521-527.
Levick et al., "Treatment of Full-Thickness Burns with Travase: Results of a Clinical Trial," Burns (1978) 4:281-284.
Silverstein et al., "In Vitro Evaluation of Enzymatic Debridement of Burn Wound Eschar," Surgery (1973) 73:15-22.
Harris et al., "The Effect of Travase on Wound Healing," Texas Reports on Biology and Medicine (1973) 31:771-776.
Merkel et al., "Collagenolytic Activity of Some Marine Bacteria," Applied Microbiology (1975) 29:145-151.
Pennisi et al., "The Combined Efficacy of Travase and Silver Sulphadizine in the Acute Burn," Burns (1976) 169-172.
Wilkes et al., "Aeromonos Neutral Proteases," Methods in Enzymology (1976) 33:404-415.

Primary Examiner—Robert A. Wax
Assistant Examiner—Gabriele E. Bugaisky
Attorney, Agent, or Firm—Vanessa L. Appleby; Jill H. Krafte; Steven T. Trinker

[57] ABSTRACT

Compositions and methods of use are provided for debriding and wound healing applications. The compositions contain certain proteases produced by microorganisms of the genus Vibrio.

27 Claims, 10 Drawing Sheets

```
GGAAACCGATTCAAACAATGAAACGAGTTGTTTTGCCAAATGGCAAAGTGAAAGTTCGTTATCAACAAACTCACCACCGGTCTACCGGTTTTCAACACC                500
----+----|----+----|----+----|----+----|----+----|----+----|----+----|----+----|----+----|----+----|
CCTTTGGCTAAGTTTGTTACTTTGCTCAACAAACGGTTTACCGTTTCACTTCAAGCAATAGTTGTTTGAGTGGTGTGCCAGATGGCCAAAGTTGTGG
 e  t  g  f  k  q  m  k  r  v  v  l  p  n  g  k  v  k  v  r  y  g  g  t  h  h  g  l  p  v  f  n  t

TCGGTAGTGGCGACTGAATCGAAGTCTGTGTAGTAGCGAAGTGTTCGGTGTGATGGCTCAGGGTATCGCAGACGTGTCTACACTGACGCGCCATCCGTTG                600
----+----|----+----|----+----|----+----|----+----|----+----|----+----|----+----|----+----|----+----|
AGCCATCACCGCTGACTTAGCTTCAGACCATCATCGCTTCACAAGCCACACTACCGAGTCCCATAGCGTCTGCTGCACAGATGTGACTGCGGTAGGCAAC
 s  v  v  a  t  e  s  k  s  g  s  s  e  v  f  g  v  m  a  g  g  i  a  d  d  v  s  t  l  t  p  s  v  e

AGATGAAGCAGGCCATTCAATTGCTAAATCGCGTTCCAACAGCAAGAAAAATGGTTGCGGAACCTGCAACGGAAACGAAAAAGCCGAGTTGATGGT                700
----+----|----+----|----+----|----+----|----+----|----+----|----+----|----+----|----+----|----+----|
TCTACTTCGTCCGGTAAAGTTAACGATTTAGCGCAAGGTTGTCGTTCTTTTTTACCAACGCCTTGACGTTGCCTTTGCTTTTGCGGCTCAACTACCA
 m  k  q  a  i  s  i  a  k  s  r  f  g  q  q  e  k  m  v  a  e  p  a  t  e  n  e  k  a  e  l  m  v

TCGTCTCGGACGACAACAATCAAGGCGCAACTAGTGTATCTGGTTGATTTCTTCGTTGCCGAGGATCACCCAGCCGCTCCTTTCTTTTTCATTGATGCCAA                800
----+----|----+----|----+----|----+----|----+----|----+----|----+----|----+----|----+----|----+----|
AGCAGACCTGCTGTTGTTAGTTCCGCTTGATCACATAGACCAACTAAAGAAGCAACGCTCCTAGTGGTGCGCAGGAAAGAAAAAGTAACTACGCGTT
 r  l  d  d  n  n  g  a  q  l  v  y  l  v  d  f  f  v  a  e  d  h  p  a  r  p  f  f  f  i  d  a  q
```

FIGURE 1C

```
                                                                                              900
ACGGGTGAAGTACTGCAAACTGGATGGTCTGAACCATGCACAAGCTGACGGTACTGGCCCTGGCCGTAACACCAAACAGTCGTTATGAATACGGTT
---+---------+---------+---------+---------+---------+---------+---------+---------+---------+
TGCCCACTTCATGACGTTTGACCTACCAGACTTGGTACGTTCGACTGCCATGACCGGCCATTGTGGTTTGTCAGCAATACTTATGCCAA t  g  e  v  l  q  t  w  d  g  l  n  h  a  q  a  d  g  t  g  p  g  g  n  t  k  t  g  r  y  e  y  g  s

1000
CTGACTTCCTCCGTTGTCATCGATAAAGTCGGCACTAAGTGTTCAATGAACAACAGCGCGGTAAGAACGGTGACCTGAACGGCTCAACTTCAGTAA
---+---------+---------+---------+---------+---------+---------+---------+---------+---------+
GACTGAAGGAGGCAAACAGTAGCTATTCAGCCGTGATTCACAAGTTACTTGTTGTCGCGCCATTCTTGCCAACTGACTTGCCGAGTTGAAGTCATT d  f  p  p  f  v  i  d  k  v  g  t  k  c  s  m  n  n  s  a  v  r  t  v  d  l  n  g  s  t  s  g  n

1100
CACCACTTACAGCTATACCTGTAACGACTCAACCAACTACAACGATTACAAAGCCATTAACGGCGCTACTCGCCACTGAACGATGCCCACTACTTCGT
---+---------+---------+---------+---------+---------+---------+---------+---------+---------+
GTGGTGAATGTCGATATGACATTGCTGAGTTGGTTGATGTTGCTAATGTTTCGGTAATTGCCGCGATGAGCGGTGACTTGCTACGGTGATGAAGCCA t  t  y  s  y  t  c  n  d  s  t  n  y  n  d  y  k  a  i  n  g  a  y  s  p  l  n  d  a  h  y  f  g

1200
AAAGTGGTTTTCGATATGTACAAAGACTGGATGAACACTACACCACTGAGCGTTCCAGCTGACTATGCCGTGTTCACTATGTAACAACTACGAAAACGCGT
---+---------+---------+---------+---------+---------+---------+---------+---------+---------+
TTTCACCAAAAGCTATACATGTTTCTGACCTACTTGTGGTGACTCGCAAGGTCGACACTGATACCGACACTGATACCATTGTTGATGCTTTTGCCA k  v  v  f  d  m  y  k  d  w  m  n  t  t  p  l  t  f  g  l  t  m  r  v  h  y  g  n  n  y  e  n  a  f
```

FIGURE 1D

```
                                                                                         1300
TCTGGAATGGTTCATCCATGACCTTCGGTGATGGCTACAGCACCTTCTACCCGCTGGTGATATTAACGTTAGTGCCCACGAAGTGAGCCACGGTTCAC
----+----|----+----|----+----|----+----|----+----|----+----|----+----|----+----|----+----|----+----|
AGACCTTACCAAGTAGGTACTGGAAGCCACTACCGATGTCGTTGGAAGATGGGCGACCACCTATAATTGCAATCACGGTGCTTCACTCGGTGCCAAGTG w  n  g  s  s  m  t  f  g  d  g  y  s  t  f  y  p  l  v  d  i  n  v  s  a  h  e  v  s  h  g  f  t

1400
CGAACAAAACTCGGGTCTGGTGTACGAGAATATGTCTGGTGGTATGAACGAAGCGTTCTCTGATATTGCAGGTGAAGCAGAGTTCTACATGAAAGGC
----+----|----+----|----+----|----+----|----+----|----+----|----+----|----+----|----+----|----+----|
GCTTGTTTTGAGCCCAGACCACATGCTCTTATACAGACCACCATACTTGCTTCGCAAGAGACTATAACGTCCACTTCGTCTCAAGATGTACTTTCCG e  q  n  s  g  l  v  y  e  n  m  s  g  g  m  n  e  a  f  s  d  i  a  g  e  a  a  e  f  y  m  k  g

1500
AGCGTTGACTGGGTTGTCGGTGCGGATATCTTCAAATCATCCGGCGGTCTGCGTTACTTTGATCAGCCTTCGCGTGACGGCCGTTCTATCGACCATGCGT
----+----|----+----|----+----|----+----|----+----|----+----|----+----|----+----|----+----|----+----|
TCGCAACTGACCCAACAGCCACGCCTATAGAAGTTTAGTAGGCCGCCAGACGCAATGAAACTAGTCGAAGCGCACTGCCGGCAAGATAGCTGGTACGCA s  v  d  w  v  v  g  a  d  i  f  k  s  s  g  g  l  r  y  f  d  q  p  s  r  d  g  r  s  i  d  h  a  s

1600
CTGACTACTACAATGCCTGAATGTTCACTACTCAAGTGGTGTATTCAACGTGCGTTCTACCTGCGTGGCTAACAAAGCGGGTTGGGATGTACGCAAAGG
----+----|----+----|----+----|----+----|----+----|----+----|----+----|----+----|----+----|----+----|
GACTGATGATGTTACCGGACTTACAAGTGATGAGTTCACCACATAAGTTGCACGCAAGATGACGACCGATTGTTGCCCAACCTACATGCGTTTCC d  y  y  n  g  l  n  v  h  y  s  s  g  v  f  n  r  a  f  y  l  l  a  n  k  a  g  w  d  v  r  k  g
```

FIGURE 1E

```
CTTTGAAGTGTTTACCCTGGCTAACCAATTGTACTGGACAGCGGAACAGCACATTTGATGAAGGCGGTTGTGTGTAGTGAAAGCTGCGAGGGACATGGGT        1700
-----+---------+---------+---------+---------+---------+---------+---------+---------+---------+
GAAACTTCACAAATGGGACCGATTGGTTAACATGACCTGTTCGCTTGTCGTGTAAACTACTTCCGCCAACACCATCACTTTCGACGCTCGCTGTACCCA
     f e v f t l a n g l y w t a n s t f d e g g c g v v k a a s d m g

TACAGCGGTTGCAGACGTAGAAGATGCGTTAACACGGTAGGCGTTAACGCGTCTCTTGTGTGCAACTCCTCCGTCTGGCGATGTACTGAAATGGTA        1800
-----+---------+---------+---------+---------+---------+---------+---------+---------+---------+
ATGTCGCAACGTCTCTGCATCTCTTCTACGCAATTGTGCCATCCGCAATTGCCAGAACACCACGTTGAGGAGGCAGAGCGCTACATGACCTTTAGCCAT
   y s v a d v e d a f n t v g v n a s c g a t p p p s g d v l e i g k

AACCGCTGCGGAACCTTCAGTAACGCCAATGACATGACTTACTACACGTTCACACCAAGCAGCTCATCTAGTGATTAAGATCACTGGCGGTAC        1900
-----+---------+---------+---------+---------+---------+---------+---------+---------+---------+
TTGGCGACCGCTTGGAAAGTCATTGCGGTTACTGTACTGAATGATGTGCAAGTGGTTCGTCGAGTAGATCGCATCACTAATTCTAGTGACCGCATG
    p l a n l s g n r n d m t y y t f t p s s s s v v i k i t g g t

AGGTGATGCAGACCTTTACGTGAAAGCGGGTAGCAAGCCAACCACCAGACTTCTTACGATTGCCGTCCATATAAGTATGTAACGAAGAGCAGTGTTCAATT        2000
-----+---------+---------+---------+---------+---------+---------+---------+---------+---------+
TCCACTACGTCTGGAAATGCACTTGCCCATGCGTTCGGTTGCTGAAGAATGCTAACGGCCAGTATATTCATACCATTGCTTCTCGTCACAAGTTAA
   g d a d l y v k a g s k p t t t s y d c r p y k y g n e e g c s i
```

FIGURE 1F

```
                                                                            2100
TCAGCGCAAGCGGGTACTACGTATCACGTTATGCTGGTGGTTACAGCAATTACGCTGGTGTGTAACTTTGCGTGTGCTGACTAAACTTCAGAATGGAACCAGTG
    ---+---------+---------+---------+---------+---------+---------+---------+---------+---------+----
AGTCGCGTTCGCCCATGATGCATATGCAATACGACGACCAATGTCGTTAATGCGACCACCAATGCGAAACGACGACTGATTTGAGTCTTACCTTGGTCAC s  a  q  g  t  t  y  h  v  m  l  r  g  y  s  n  y  a  g  v  t  l  r  a  d  .  t  q  n  g  t  s  e

2200
AAGGCGCACCTTAAGGTCGCCCTTTTTGTATCAGGCGATCTGTGTAAACGTGACCTGATCGAAGTGAGGATTGGCCGCCAGGCGCTTGCATGCTGTGTAAG
    ---+---------+---------+---------+---------+---------+---------+---------+---------+---------+----
TTCCGCGTGGAATTCCAGCGGGAAAAACATAGTCCGCTAGACACATTTGCACTGGACTAGTTCACTCCTAACCGGCGGTCGCGAACGTACGACACATTC g  a  p  .  g  r  l  f  c  i  r  r  s  v  .  t  .  p  d  r  s  e  d  w  p  p  a  l  a  c  c  v  r

2300
GACTCGGTGGGCAACGTCTCATGGCCACTGGATGTGCAATGACGATGCCCTCTTTTCGTTCTGTGGTGTATGTTGTATCGACCGCCGTCCCTTCCACAA
    ---+---------+---------+---------+---------+---------+---------+---------+---------+---------+----
CTGAGCCACCCGTTGCAGAGTACCGGTGACTGACCGGTGACCTACGCGTTACTGCTACGGGAGAAAAGCAAGACACCACATAGCTGGGCAGGGAAGGTGTT t  r  w  a  t  s  h  g  h  w  m  s  q  .  r  w  p  l  f  v  l  w  c  m  l  y  r  p  p  s  l  p  q

TCGTGCCGTTGAGCAGTTTGAGTCTGACTGGCAGGTGATAAAGGCAGGCAATCTCGATGTAATCGTACTGGCTGCAG     2377
    ---+---------+---------+---------+---------+---------+---------+---------+---
AGCACGGCAACTCGTCAAACTCAGACTGAGACTGACCGTCCACTATTTCCGTCCGTTAGAGCTACATTAGCATGACCGACGTC s  c  r  .  a  v  .  v  .  l  a  g  d  k  g  r  g  s  r  c  n  r  t  g  c  s
```

COMPOSITIONS CONTAINING PROTEASE PRODUCED BY VIBRIO AND METHOD OF USE IN DEBRIDEMENT AND WOUND HEALING

TECHNICAL FIELD

The present invention relates to debriding compositions and to methods using such compositions for debridement and/or wound healing, which contain certain proteases produced by microorganisms of the genus Vibrio. More particularly, the protease is capable of effectively digesting necrotic tissue while viable living tissue is not substantially injured. The protease also has wound healing properties.

BACKGROUND OF THE INVENTION

The healing of wounds is a complex process which is often further complicated by the presence of non-viable, necrotic tissue in the wound area. Debridement is the process of removing the non-viable tissue from a wound to prevent infection and facilitate healing.

Considerable efforts have been made to discover materials capable of distinguishing between viable and non-viable tissue. The discovery of materials which would digest devitalized tissue while not attacking viable tissue would make it possible to remove the devitalized tissue without surgery. It would be a beneficial therapeutic agent in virtually all disease processes where topically devitalized tissue needs to be removed from the viable organism such as burns, decubitus ulcers, pressure necroses, incisional, traumatic and pyogenic wounds, and ulcers secondary to peripheral vascular disease.

One area that has attracted considerable attention is the use of proteolytic enzymes and other chemicals to effect the early debridement of eschar tissue, resulting from burns. Such devitalized tissue is an excellent culture medium and the principal source of the septicemia which is the proximate cause of death in the majority of severely burned patients.

In burns, the devitalized tissue is referred to as eschar. Burn eschar is a complex mixture of dried blood, purulent exudates, and denatured proteins normally found in the epidermal and dermal skin layers. The denatured proteins found in eschar are primarily collagen, elastin, fibrin, hemoglobin, and other coagulated proteins.

For a proteolytic enzyme to be most useful as a debriding agent, particularly for burns, it is desirable for the protease to distinguish between viable and non-viable tissue; readily and thoroughly hydrolyze a wide variety of denatured proteins found in eschar; function at physiological pH and temperature; be compatible with adjunct therapies (e.g., cleansing agents, topical antibiotics); not interfere with normal wound healing or complicate skin grafting; and remain stable in various formulations and at a wide range of temperatures. A number of proteolytic enzyme preparations have been used as debriding agents with varying degrees of success.

Travase ® ointment, which is a preparation containing proteolytic enzymes obtained from sterile filtrates of *Bacillus subtilis*, is another known enzymatic debriding agent (Garrett, *Clinical Medicine* (1969) 76:11-15) and U.S. Pat. No. 3,409,719. Crikelair (U.S. Pat. No. 4,276,281) describes the use of elastase, a serine protease derived from pancreas, as an enzymatic debridement agent. Klein et al. (U.S. Pat. No. 4,329,430) describe a proteolytic enzyme mixture derived from bromelin which is useful for the digestion, dissection and separation of non-viable, devitalized tissue. Schmitt (U.S. Pat. No. 3,983,209) teaches treating burns in animals by applying enzymes to a burn surface for debridement of eschar and necrotic tissue. The enzymes disclosed included papain, trypsin, lysozyme, streptokinase, fibrinolysin, pinguinain, Travase and bromelain in a specified hydrophobic polymer. Bioerosion over prolonged periods of time slowly released the proteolytic enzymes.

Merkel (U.S. Pat. No. 3,677,900) discloses that collagenases, especially those produced by a species of Vibrio, are useful as debriding agents. However, Merkel's collagenase is an enzyme capable of digesting native, undenatured collagen under physiological conditions of pH and temperature and is not inhibited by serum. The Merkel collagenase therefore is not likely to distinguish between viable and non-viable tissue. Collagenases also have a very narrow substrate specificity. Further, collagenase has been reported to cause significant damage to viable dermal tissue, causing reduced granulation tissue development and wound maturation (Hamit et al., Ann. Surg. (1960) 151:589).

While other proteolytic debriding agents are known, many of these agents have been shown to be ineffective and cause local or systemic toxicity. None of the previous proteolytic debriding agents have the superior characteristics of the present invention, including the ability to act as a wound healing agent.

SUMMARY OF THE INVENTION

This invention provides compositions for debriding wounds comprising a pharmaceutically acceptable topical carrier admixed with an effective amount of a protease selected from the group consisting of (a) an extracellular neutral protease produced by cultivation of a microorganism belonging to the genus Vibrio characterized by the following properties:
  i. hydrolyzes components of necrotic tissue including denatured collagen, elastin and fibrin;
  ii. does not substantially hydrolyze native tissue in vivo; and
  iii. exhibits about 80% to about 95% activity when stored at 25° C. in a topical formulation.

(b) a protease expressed by recombinant host cells which have been transformed or transfected with an expression vector for said protease (a); and (c) mutants and hybrids of proteases (a) and (b) which are characterized by the properties (i) to (ii).

Also provided are methods of debriding wounds which comprise contacting a wound with an effective amount of such Vibrio protease-containing compositions. It is a primary object of this invention to provide compositions and methods of debriding wounds wherein the active ingredient is a protease isolated from the Vibrio strain *Vibrio proteolyticus* ATCC 53559. Further, said protease has a DNA sequence as illustrated in FIG. 1.

It is a further object to provide compositions for debriding wounds wherein the pharmaceutically acceptable topical carrier is either hydrophobic or hydrophilic. Hydrophilic formulations are particularly preferred. The compositions demonstrate substantial enzyme stability when stored at 25° C.

Another object is the ability of the compositions and methods of the invention to have debriding effects on a wide variety of wounds including, but not limited to, management of full and partial thickness burn wounds; debridement of ulcerative lesions, principally pressure (decubitus) ulcers and varicose, stasis and trophic ulcers; preparation of skin graft sites and general surgical wounds such as amputation, incisional, traumatic and pyogenic wounds; treatment of vaginitis, cervicitis, circumcisions, episitomy, pilonidal cyst wounds, wounds, carbuncles, sunburn, frostbite, and cataract scar tissue.

A further object of the invention is to provide compositions and methods which have wound healing properties. Wound healing properties include ability to increase the rate at which wounds heal and also the ability to improve wound healing (i.e., maintain response to tactile stimulus, less scarring, improved neovasculorization, etc.). Wound healing can be divided into four essential components: inflammation, angiogenesis, collagen deposition and epithelialization. All of these play a role in the healing of all wounds. Particularly, the compositions of the invention exhibit the ability to cause wound contracture.

BRIEF DESCRIPTION OF THE DRAWINGS

FIG. 1 (6 pages) is a representation of the DNA sequence of the vibriolysin gene. The DNA sequence illustrated comprises a portion of a 6.7 kb Hind III fragment of the Vibrio -proteolytious gene (described in U.S. Pat. No. 4,966,846, which encodes vibriolysin. An open reading frame exists from approximately base 249-2078, within which the DNA region encoding vibriolysin is found.

DETAILED DESCRIPTION OF THE INVENTION

Figure 2:
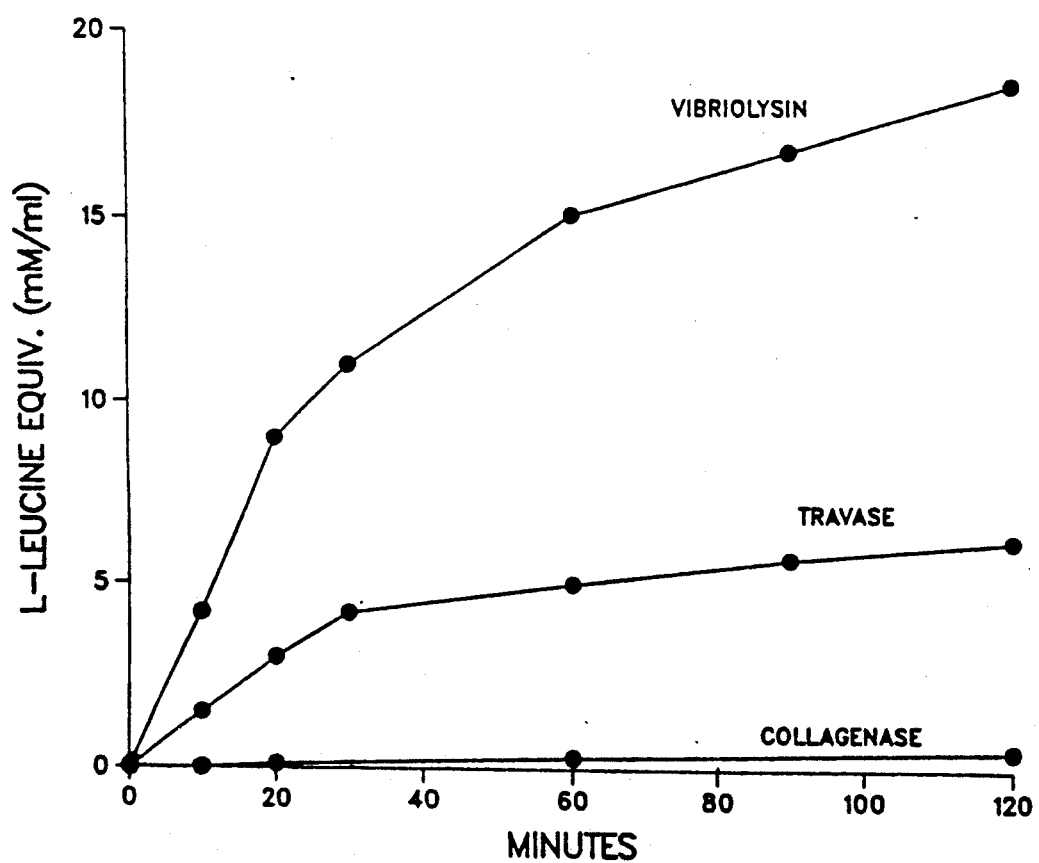
FIG. 2 compares the ability of vibriolysin, Travase, and collagenase to act on the substrate fibrin.

The proteases of this invention are characterized by a combination of properties which renders them ideal candidates for use in wound debridement applications. By way of illustration and not limitation, such properties include:

i. hydrolyzes components of necrotic tissue including denatured collagen, elastin and fibrin;
ii. does not substantially hydrolyze native tissue in vivo; and
iii. exhibits about 80% to about 95% activity when stored at 25° C. in a topical formulation.

The proteases of the invention are capable of distinguishing between viable and non-viable, necrotic tissue and are also active for sustained periods in formulations which are unacceptable to other proteases.

For the purposes of this application and the appended claims, the aforementioned properties of the proteases of this invention are determined as follows: For initial in vitro efficacy studies with the proteases of this invention, constituent proteins associated with eschar (e.g., denatured collagen, fibrin, denatured elastin) and native tissue were subjected to enzymatic hydrolysis. For comparison, the proteases (sutilains) derived from *Bacillus subtilis* were used. These proteases are formulated into a hydrophobic base and distributed commercially as Travase TM ointment (Boots-distributed Flint Laboratories, Morton Grove, IL). The proteases from Travase ointment were extracted as described in official monographs of the United States Pharmacopoeia XXII (1990; p. 1306) and will henceforth be referred to as Travase proteases. For assessment of hydrolysis of each substrate, vibriolysin and Travase proteases were added to each reaction mixture to an equivalent activity unit basis as determined by the azocasein assay described below.

A. Azocasein Hydrolysis

Azocasein is a readily available protein that is used as a standard for measuring protease activity. A sample of protease is incubated for ten minutes at 37° C. in 50 mM Tris-HCl buffer (pH 7.4) containing 1.0 mg/ml of azocasein (sulfanilamideazocasein, Sigma Corp., St. Louis, MO) with a final volume of 0.5 ml. At the end of this incubation period, 0.5 ml of 10% w/v trichloroacetic acid are added and immediately mixed and the resulting mixture is then stored on ice for 10 minutes. The mixture is then centrifuged and the optical density of the resulting supernatant is determined at 420 nm against a blank that contains either no enzyme or inactivated enzyme in the buffered azocasein solution. One unit of activity is defined as the amount of enzyme required to cause a change in absorbance of 2.5 at 420 nm.

B. Ninhydrin Assay

Nonspecific hydrolysis of various substrates resulting in the release of peptides and free amino acids was measured by the ninhydrin method (*Moore and Stein. J. Biol. Chem.* (1948)176:367) as described by a modification of the procedure of Mandl et al. (*J. Clin. Invest.* (1953) 32:1323). Fifty to one hundred microliters of clarified hydrolysis sample were added to a 1.0 ml mixture containing 0.5 ml of 4% ninhydrin in methylcellusolve and 0.5 ml of 0.2 M citric acid (pH 5.0 containing 7.1 mM stannous chloride). The solution was boiled for 20 minutes, then chilled in an ice bath. Fifty microliters wer added to 1.0 ml 50% n-propanol and the absorbance of the solution was read in a Shimadzu Spectrophotometer at 600 nm against a water blank. Leucine was used as a reference standard.

Preparation of the Protease

The proteases of this invention are produced by fermentation of a suitable Vibrio species in a nutrient medium and then recovering the protease from the resulting broth. Fermentation is conducted aerobically in, for example, a casein hydrolysate, NZ-amine B, or soy flour nutrient medium containing inorganic salts such as sea salts, sodium sulfate, potassium dihydrogen phosphate, magnesium sulfate and certain trace elements at a pH of from about 8.0 to 8.6, preferably from about pH 8.4 to 8.6, and at a temperature of from about 25° to 30° C., e.g., about 27° C., until the culture reaches early stationary phase growth.

The enzyme may thereafter be recovered from the fermentation broth by conventional procedures. Typically, the broth is first centrifuged or filtered to separate the cell portion and insoluble material. Thereafter, the supernatant is concentrated by, e.g., ultrafiltration. The resulting ultrafiltrate may be used as is or may be precipitated with organic solvents such as acetone or inorganic salts such as ammonium sulfate, followed by centrifugation, ion-exchange chromatography or filtration in order to isolate an enzyme useful in debriding compositions. The protease is also stable when lyophilized. Other procedures such as are routine to those skilled in the art may also be used to cultivate the Vibrio microorganism and to recover the protease of this invention therefrom.

Figure 1A:
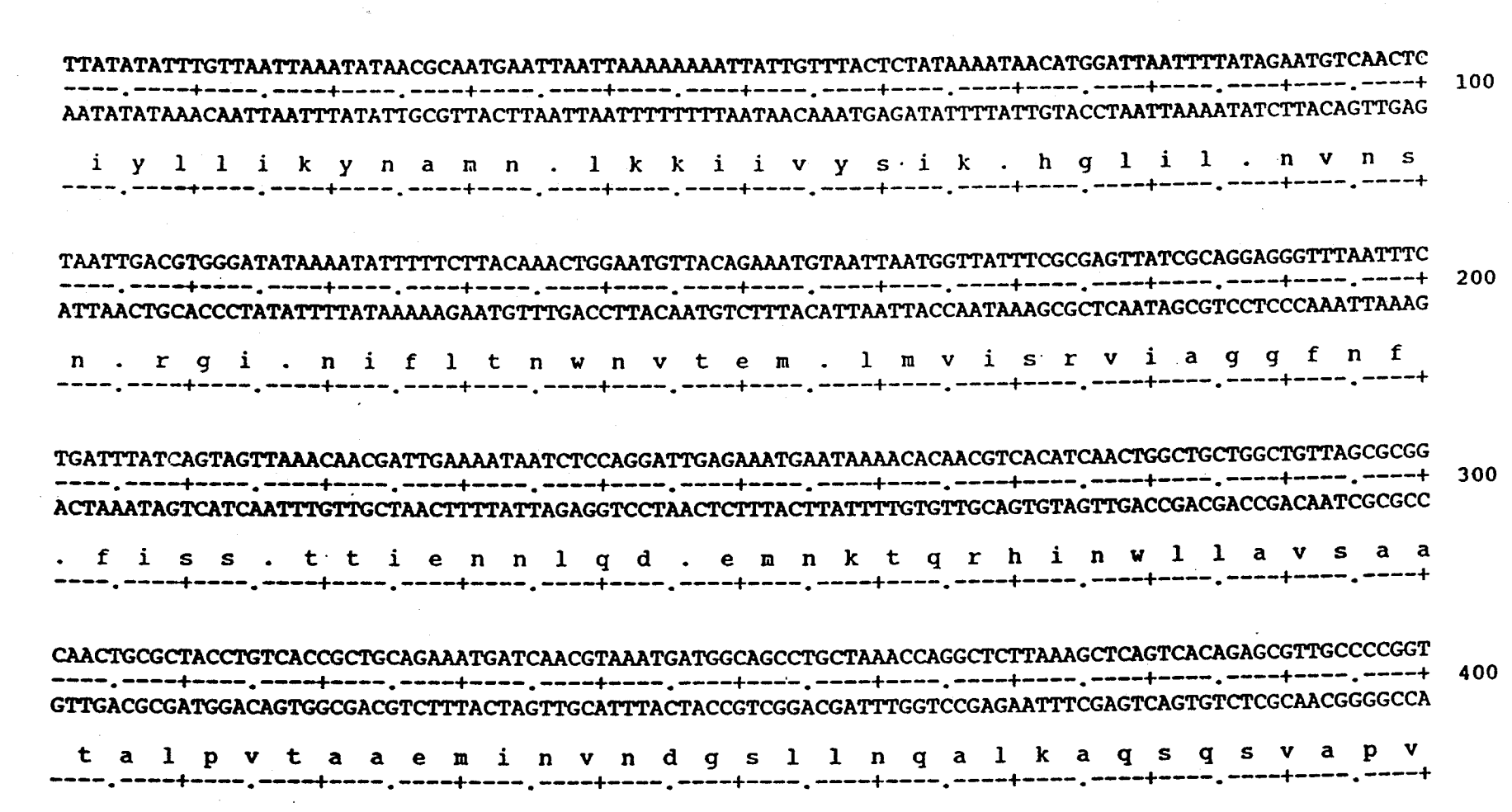

Useful microorganisms for use as a source of the instant proteases may comprise any suitable Vibrio, eromonas, Pseudomonas, Serratia or Bacillus or other marine microorganism species which seoretes a protease having the above properties. A particularly preferred microorganism for this purpose is *Vibrio proteolyticus (ATCC 53559)*. A viable culture of this microorganism has been irrevocably deposited with the American Type Culture Collection (ATCC), 12301 Parklawn Drive, Rockville, MD 20852, with no restrictions as to availability, and W. R. Grace & Co.-Conn., the assignee hereof, assures permanent availability of the culture to the public through ATCC upon the grant hereof. The DNA sequence of the protease secreted by *Vibrio proteolyticus* (ATCC 53559), referred to herein as vibriolysin, is set forth in FIG. 1. While *Vibrio proteolyticus* (ATCC 53559) comprises the preferred protease source, other species of useful Vibrio microorganisms can readily be identified by those skilled in the art by screening the proteases produced thereby using the procedures set forth above.

In addition to the direct cultivation of a Vibrio species, the proteases of this invention may also be prepared by the cultivation of recombinant host cells which have been transformed or transfected with a suitable expression vector with an insert containing the structural gene for the Vibrio-derived proteases of this invention. Such procedures may be desirable, for example, in order to increase protease yields over that obtained with the wild type Vibrio microorganism or in order to produce improved mutant proteases.

Techniques for the cloning of proteases are well known to those skilled in the art of recombinant DNA technology, and any suitable cloning procedure may be employed for the preparation of the proteases of this invention. Such procedures are described, for example, in U.S. Pat. No. 4,468,464; European Published Patent Application No. 0 130,756; PCT Published Patent Application No. WO 87/04461; and Loffler, Food Technology, pages 64–70 (Jan. 1986); the entirety of which are hereby incorporated by reference and relied on in their entirety.

A particularly preferred procedure for cloning the Vibrio proteases of this invention is described in commonly assigned U.S. Pat. No. 4,966,846, the entirety of which is hereby incorporated by reference and relied on in its entirety. According to the procedure of this patent, a gene library is first prepared, using the DNA of Vibrio source cells which have been determined by the assays described above to synthesize the proteases of this invention. Chromosomal DNA is extracted from the Vibrio source cells and digested with restriction enzymes by known procedures to give cleavage of the DNA into large fragments. Partial digestion with Sau3A is preferred, although other restriction enzymes (e.g., MboI, BamHI, etc.) may be used. The DNA fragments are then ligated into vectors suitable for allowing isolation of clones which express the protease enzyme. A preferred vector for this purpose is BamHI digested *E. coli* cosmid vector pHC79 (Bethesda Research Laboratories). The recombinant vectors (i.e., pHC79 cosmids containing DNA fragments from the protease-containing genome) are than packaged into bacteriophage particles, preferably bacteriophage lambda, thereby producing a gene library in bacteriophage lambda particles. For production of a gene library in bacteriophage, a cosmid vector or lambda vector is used. In other cases, plasmid vectors may be used.

The resultant bacteriophage particles are then used to insert the gene library DNA fragments into suitable gram-negative host cells. Preferably, the recombinant bacteriophage particles are used to transect *E. coli*, such as, for example, *E. coli* strain HB101, although other strains of *E. coli* may be used if desired. Since *E. coli* strains do not naturally synthesize an extracellar neutral protease enzyme, the *E. coli* clones easily may be evaluated for the presence and expression of the protease gene by the assays described below.

It is known that colonies of Vibrio which synthesize protease enzyme will produce a zone of clearing on milk agar plates due to the proteolytic hydrolysis of the casein component of milk. Non-recombinant *E. coli* colonies do not secrete a protease naturally. Thus, *E. coli* clomes of this invention which contain the protease gene are therefore readily identified by this assay. This milk-clearing assay is preferred for use with *E. coli* and other host strains which do not naturally produce an extracellular protease. Other gram-negative and gram-positive strains may be used as hosts.

Confirmation may be made by using other protease assays. For example, clones may be confirmed for expression of the protease enzyme by demonstrating that the fermentation broths of these clones are capable of hydrolyzing substrates such as Hide powder azure, azocoll or N-[3-(2-furyl)acryloyl]-alanyl-phenylalaniamide (FAAPA). Alternatively, these assays may be used in the first instance to identify the protease gene-containing clones.

It is significant in two respects that expression of the neutral protease gene in *E. coli* and other "non-secreting" hosts (that is, hosts which do not naturally secrete a protease) can be detected as a zone of clearing on a milk agar plate. First, this is evidence that the active, functional enzyme is being synthesized by the gram-negative host. Second, the extracellular presence of protease on the milk agar plates is evidence that the enzyme is being externalized in some manner, either by secretion or by cell lysis. Since *E. coli* and some other gram-negative bacteria normally do not secrete significant quantities of proteases into the media, this is important in terms of the ability to recover protease enzymes produced as a result of expression of Vibrio protease genes in these non-secreting hosts.

Also contemplated for use herein are mutants and hybrids of the foregoing proteases which substantially retain the preferred performance characteristics. As used herein, the term "mutant" refers to a protease in which a change is present in the amino acid sequence as compared with wild type or parent enzymes. "Hybrid" refers to genetically engineered proteases which combine amino acid sequences from two or more parent enzymes and exhibit characteristics common to both.

Techniques for the preparation of mutant proteases are well known to those skilled in the art and include exposure of a microorganism to radiation or chemicals and site-directed mutagenesis. Mutagenesis by radiation or chemicals is essentially a random process and can require a tedious selection and screening to identify microorganisms which produce enzymes having the desired characteristics. Preferred mutant enzymes for the purposes of this invention are thus prepared by site directed mutagenesis. This procedure involves modification of the enzyme gene such that substitutions, deletions, and/or insertions of at least one amino acid at a predetermined site are produced in the protease enzyme. Techniques for site directed mutagenesis are well known to those skilled in the art and are described, for example, in European Published Patent Application No. 0 130,756 and PCT Published Patent Application No. W087/04461, the entirety of which are hereby incorporated by reference and relied on in their entirety.

In one such procedure, known as cassette mutagenesis, silent restriction sites are introduced into the protease gene, closely flanking the target codon or codons. Duplex synthetic oligonucleotide cassettes are than ligated into the gap between the restriction sites. The cassettes are engineered to restore the coding sequence in the gap and to introduce an altered codon at the target codon.

The use of such procedures on the parent Vibrio proteases may be desirable in order to improve the properties of the wild type or parent protease. For example, the methionine, histidine, cysteine or tryptophan residues in or around the active site of the protease may be replaced in order to improve stability to chemical oxidation, as suggested in Estell et al., *J Biological Chemistry*, Vol. 260, No. 11, pages 2518–2521 (1985).

Hybrids of the parent or wild type proteases may likewise be prepared by known protein engineering procedures analogous to the above-discussed cassette mutagenesis procedure by ligating a region of the gene of one parent enzyme (which need not be derived from Vibrio) into the gene of a second parent enzyme.

Formulation and Administration

Formulations of the debriding protease using available excipients and carriers are prepared according to standard methods known to those in the art. The protease can be formulated in ointments, lotions, gels, pastes, foams, aerosols, or immobilized on beads. The protease can also be immobilized in a wound dressing, tape or gauze. The enzyme formulations can be either hydrophilic or hydrophobic. Examples of hydrophobic bases include parafin-mineral oil, and hydrophilic bases include petrolatum-propylene glycol-water bases. Hydrophilic formulations are preferred, particularly if the enzyme is stable in the formulation during storage at room temperature. Reasons for the preference include not having to raise the temperature of the preparation before administering to the wound. More importantly, enzymes in a hydrophilic ointment should be more accessible for hydrolysis of necrotic tissue, and in contrast to a hydrophobic base, the ointment can be easily removed from the wound by washing with saline. Additional active ingredients, including antibiotics, humectants, deoxyribonucleases, fibronectin, growth factors such as fibroblast growth factor (FGF), epidermal growth factor (EGF), the transforming growth factors (TGF), insulin-like growth factors (IGF-1 and IGF-2), and/or platelet-derived growth factor (PDGF) and the like, can be included in the formulation, if desired.

Topical administration is most appropriate for wound debridement, although other routes of administration may be desirable under certain conditions. Standard topical formulations are employed using, for example, 0.01–10% protease by weight. Such formulations are applied 1–6 times per day to the affected area. The application and concentration of the ointment or other formulation depends, of course, on the severity and type of the wound and nature of the subject.

Topical administration is also appropriate in order to stimulate vascularization and healing of traumatized tissue. Substrates include burns, bone fractures, surgical abrasions such as those of plastic surgery, cuts, lacerations, bed sores, slow-healing ulcers, tendonitis, bursitis, vaginitis, cervicitis, circumcisions, episitomy, pilonidal cyst wounds, carbuncles, sunburn, frostbite.

The following abbreviations have been used throughout in describing the invention:

$HBO_3$ —boric acid
$CaCl_2$ —calcium chloride
$CaSO_4$ —calcium sulfate
cm —centimeter
$CuSO_4$ —copper sulfate
° C. —degrees Centigrade
g —gram(s)
I.M. —intramuscular
kb —kilobase pair
$MgSO_4$ —magnesium sulfate
$MnCl_2$ —manganese chloride
mg —milligram(s)
ml —milliliter(s)
mm —millimeter(s)
mM —millimolar
M —molar
mS —milli semen
nm —nanometer(s)
O.D. —optical density
% —percent
$K_2HPO_4$ —potassium phosphate
NaOH —sodium hydroxide
$Na_2MoO_3$ —sodium molybdate
$Na_2SO_4$ —sodium sulfate
$H_2O$ —water
w/v —weight to volume
$ZnSO_4$ —zinc sulfate

EXAMPLES

The following examples serve to give specific illustration of the practice of this invention, but they are not intended in any way to act to limit the scope of the invention.

EXAMPLE 1

Preparation of Vibriolysin

*V. proteolyticus* ATCC 53559 was cultured in a medium with the following composition (g or ml per liter): NZ-amine B, 40; $Na_2SO_4$, 25; dextrose, 10; $K_2HPO_4$, 4; $MgSO_4 7H_2O$, 0.4; Darastil-8270 (Dearborn), 0.1 ml and 6.1 ml of trace elements solution. The trace element solution comprises (grams per liter) the following: $ZnSO_4 7H_2O$, 18.29; $MnCl_2 \cdot 4H_2O$, 18.86; $CaSO_4 \cdot 2H_2O$, 0.91 g, $HBO_3$, 0.07; and $Na_2MoO_4 \cdot 2H_2O$, 0.04. prior to sterilization, pH was adjusted to 7.0.

*V. proteolyticus* was cultured in either 1.5- or 10-liter fermentors. Fermentors containing the aforementioned medium were inoculated with 1% (v/v) culture obtained by growing *V. proteolyticus* in shake flasks containing medium of the same composition for 20 hours. The fermentations were performed at 28° C., 1,000–1,250 rpm and an aeration of 1.0 volume of air per volume of medium per minute. The pH of the fermentation was maintained at pH 7.8 by the automatic addition of an acid and base titrant.

Growth of *V. proteolyticus* was monitored by measuring optical density at 640 nm, and protease activity was monitored by the azocasein assay described earlier. During the early stationary growth phase of the fermentation the product protease reaches titers of approximately 85,200 to 127,800 azocasein units/liter as measured by the azocasein assay described earlier. The broth was harvested by centrifugation to separate the cell portion.

The supernatant containing the proteolytic activity was concentrated using an Amicon S1OY10 spiral wound filter (Amicon Corp., Lexington, MA). The concentrate was diafiltered with 10 mM Tris buffer containing 1 mM $CaCl_2$ until the conductivity of the rententate was approximately 1 mS and the pH was neutral. This material was lyophilized and stored at $-20°$ C. until use or formulated into an ointment.

EXAMPLE 2

Fibrin Hydrolysis

Fibrin is a protein component found in wound eschar. To measure fibrinolytic activity, human plasma fibrin (Sigma) was hydrolyzed at 37° C. in a reaction vessel containing 10.0 mg. fibrin per ml of 100 mM TES (N-tris[hydroxymethyl]methyl-2-aminoethanesulfonic acid) buffer (pH 7.5) containing 0.9% NaCl and 0.1 mM $CaCl_2$. The test enzymes, vibriolysin and Travase, were added to reaction solutions to a concentration of 10 units/ml (azocasein units) with constant mixing; collagenase (0.14 mg/ml, Sigma; Type VII) was added to the reaction. Samples were removed periodically and assayed for free amino groups using the ninhydrin assay described earlier.

The rate of hydrolysis of human fibrin by vibriolysin was approximately four-fold faster than the rate observed with Travase proteases (FIG. 2). Further, the hydrolysis of fibrin was more extensive. In one hour, vibriolysin hydrolyzed 26% of the fibrin substrate as compared to 7.5% for the Travase proteases. These data are highly significant since others have reported that Travase is most effective hydrolyzing fibrin compared to other eschar component [Shakespeare, P.G. et al., *Burns* (1979), 6:15-20) Collagenase, as expected, exhibited no hydrolysis of fibrin (FIG. 2).

EXAMPLE 3

Denatured Collagen Hydrolysis

Eschar associated with deep dermal burns or ulcers has been shown to consist primarily of denatured collaoen bound to viable tissue. Thus, an effective debridement agent must digest the collagen component of necrotic tissue. To assess collagen hydrolysis two sources of collagen were used: human placental collagen (Sigma, Type IV) and Bovine achilles tendon collagen (Worthington Biochemicals). The latter substrate was heated for 2 minutes at 100° C. to denature the collagen.

For human placental collagen hydrolysis, reaction mixtures contained 2.0 mg of collagen per ml of Tris-HCl buffer (pH 7.5) containing 0.1 mM $CaCl_2$. Ten azocasein units of each test enzyme were added to each reaction mixture, pre-equilibrated at 37° C.. Collagenase (0.14 mg/ml) was also added to a reaction mixture. Samples were removed periodically, and free amino acids and small peptides were determined by the ninhydrin assay procedure described earlier.

Figure 3:
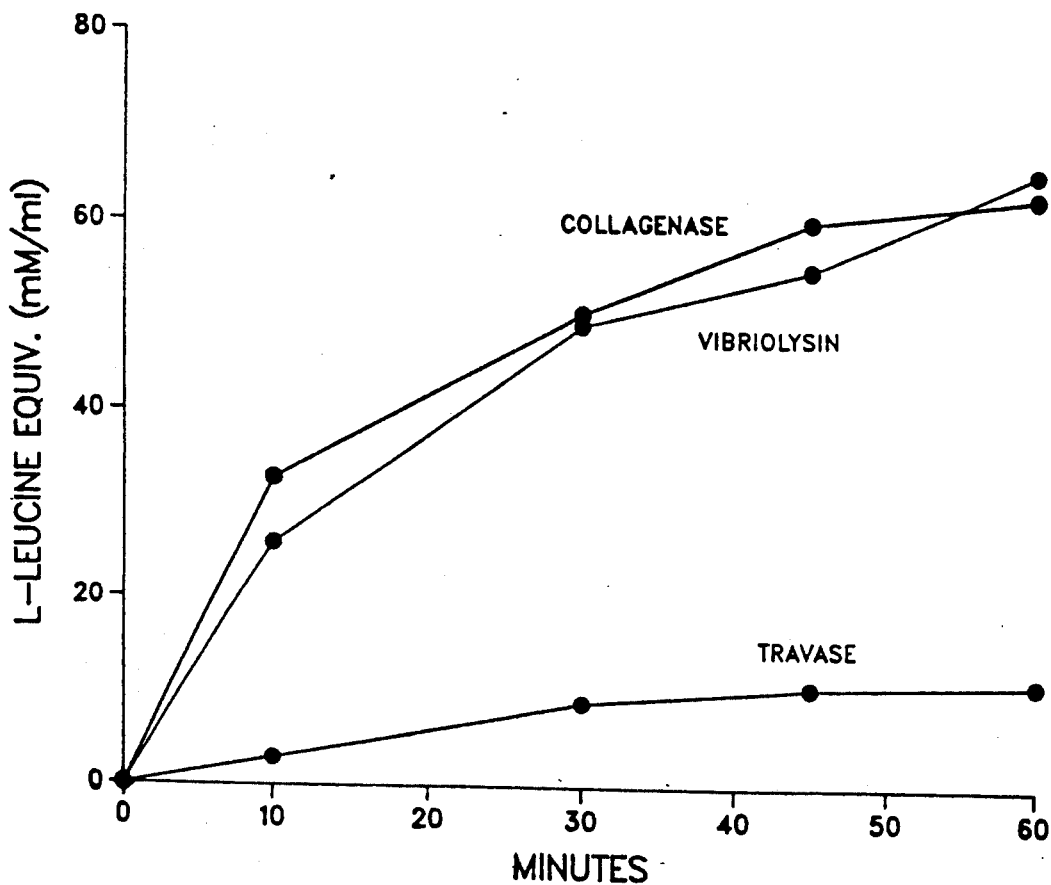
FIG. 3 compares the ability of vibriolysin, Travase, and collagenase to act on the substrate denatured collagen.

The hydrolysis of human placental collagen by vibriolysin and Travase proteases are shown in FIG. 3. The data indicate that vibriolysin exhibits superior collagen hydrolytic activity as compared to Travase proteases and is comparable in activity to collagenase.

For denatured Achilles tendon collagen hydrolysis, reaction mixtures contained 10 mg of collagen per ml of 100 mM TES buffer (pH 7.5) containing 0.9% NaCl and 0.1 mM $CaCl_2$. Five azocasein units per ml of each protease were added to reaction solutions preincubated at 37° C.; 0.1 mg of Worthington collagenase (CLSIII) was also used. The hydrolysis of collagen was determined as a function of time with the ninhydrin assay procedure described earlier. These results are summarized in Table I.

TABLE I

| Enzyme | Leucine (mM) Equivalents Liberated at Minute: | | | | |
|---|---|---|---|---|---|
| | 0 | 20 | 45 | 60 | 120 |
| Vibriolysin | 0 | 10.4 | 12.4 | 16.8 | 17.2 |
| Travase | 0 | 3.5 | 7.9 | 8.6 | 13.1 |
| Collagenase | 0 | 7.1 | 8.9 | 11.9 | 21.2 |

As noted above, vibriolysin exhibits exceptional activity toward collagen as compared to Travase proteases and digestion of collagen was comparable for collagenase and vibriolysin. The enzyme of the present invention is a more favorable therapy for burn or ulcer treatment due to its effectiveness in breaking down collagen fibers which make up tenacious devitalized wound tissue.

EXAMPLE 4

Elastin Hydrolysis

Elastin represents a minor component of human skin (3%). Hydrolysis of this substrate was determined with reaction solutions containing 6.6 mg of elastin-congo red (Sigma) per ml of 100 mM TES buffer (pH 7.5) containing 0.9% NaCl and 0.1 mM $CaCl_2$. Enzymes (vibriolysin and travase) were added to reaction solutions (37° C.) to a concentration of 5 azocasein units per milliter; 0.75 ml samples were removed periodically, added to 0.5 ml of 0.7 M Sorensons buffer (pH 6.0) and immediately centrifuged. The absorbance of the supernatants were measured at 495 nm.

Figure 4:
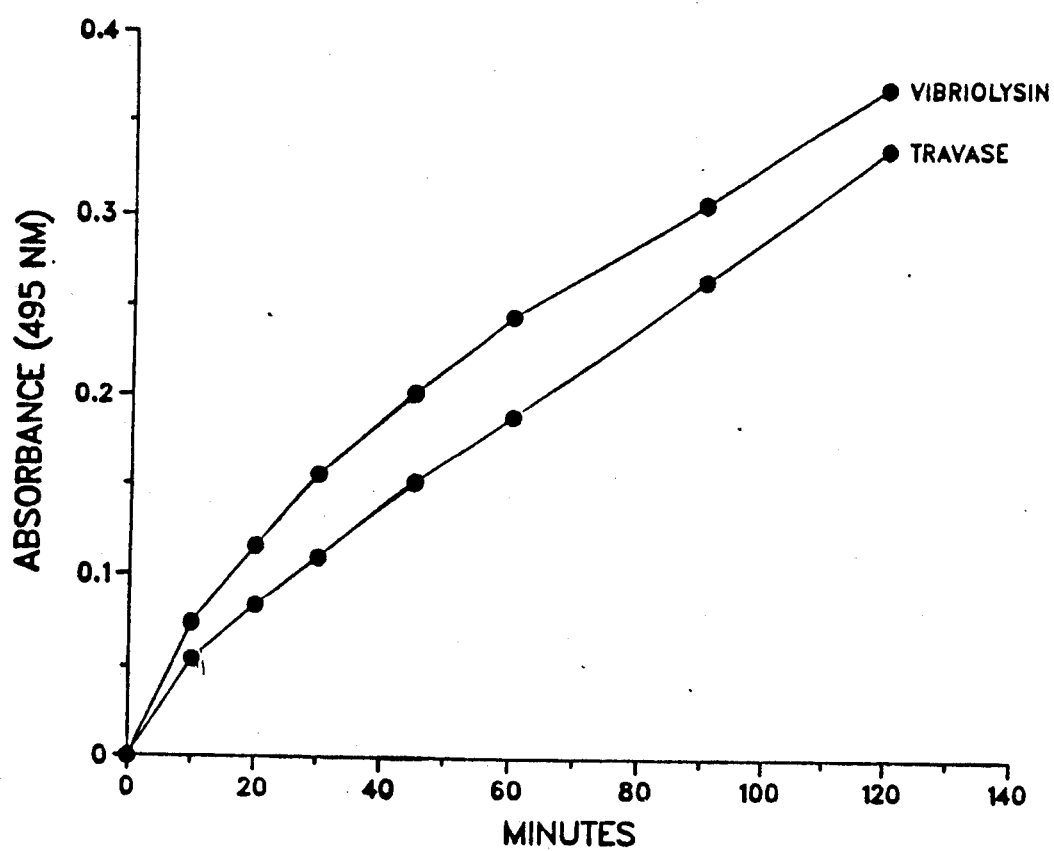
FIG. 4 compares the ability of vibriolysin and Travase to act on the substrate elastin.

The hydrolysis of elastin is shown in FIG. 4. Again, vibriolysin hydrolyses this component of necrotic tissue better than Travase proteases on an equal unit basis.

EXAMPLE 5

Shelf-Life Stability at Ambient Temperature

The shelf-life stability for vibriolysin blended into a hydrophobic and hydrophilic ointment was assessed at ambient temperature ($\sim 25°$ C.). Vibriolysin powder was blended to a concentration of 1,200 azocasein units per gram base into (1) a parafin-mineral oil base (hydrophobic) and (2) a petrolatum-propylene glycol-water base (hydrophilic). Since Travase is formulated in a hydrophobic ointment, one part of this material was mixed with one part of a hydrophilic ointment to attempt to partially simulate the hydrophilic conditions for vibriolysin.

Vibriolysin was extracted from the hydrophobic ointment as described in the USP method for extracting Travase proteases. The hydrophilic formulation was extracted directly with TES buffer. The residual proteolytic activity was then determined by hydrolysis of azocasein.

Figure 5:
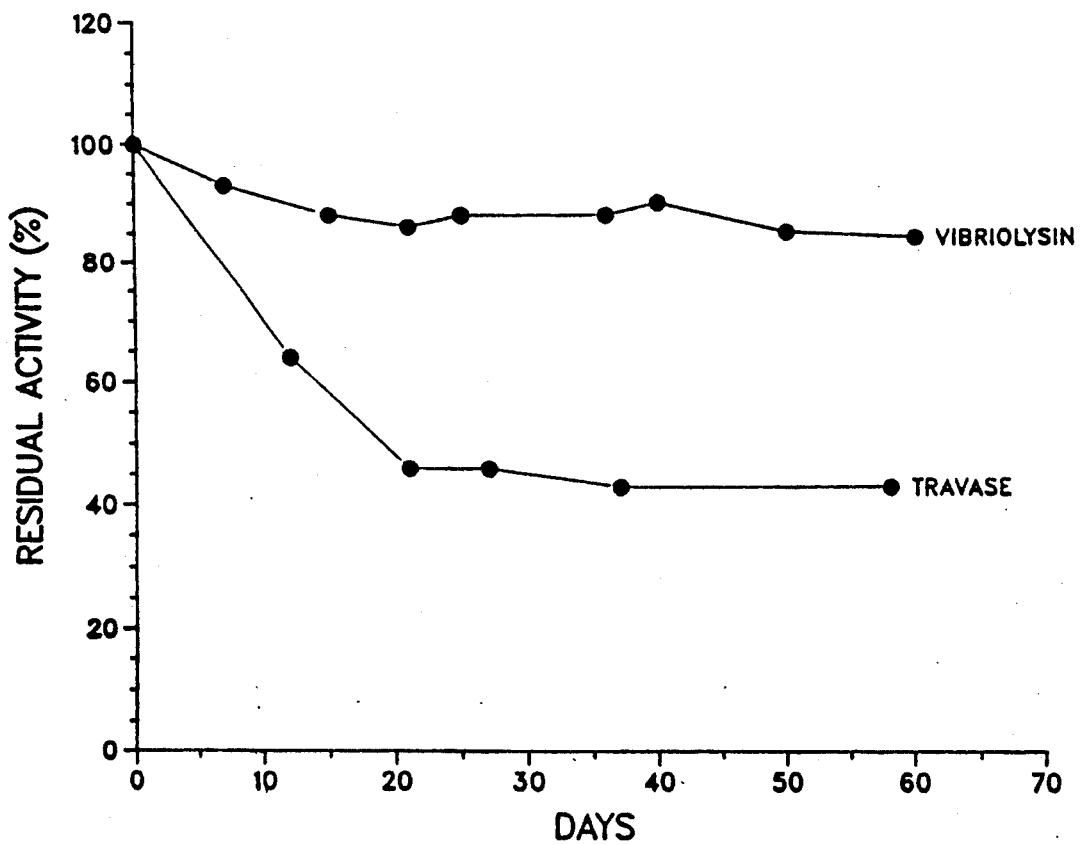
FIG. 5 compares the shelf-life stability at 25° C. of a hydrophilic vibriolysin formulation and a hydrophilic/-hydrophobic Travase formulation.

The shelf-life stability of vibriolysin in a hydrophilic base at ambient temperature, as well as the residual activity of Travase proteases in the hydrophobic-hydrophilic composite is shown in FIG. 5. The results indicate that vibriolysin has excellent stability (>80% residual activity) over the 60-day incubation period. By comparison, proteases from the Travase formulation maintained only 43% of its original activity. Both enzymes exhibited comparable shelf-life stability for a hydrophobic base at ambient temperature.

EXAMPLE 6

In Vivo Study

For in vivo assessment of the debriding properties of the protease of this invention, white domestic pigs were selected due to their morphologic and functional similarities of their skin to human skin. Accordingly, one young specific pathogen free (SPF) pig weighing 15-20 kg was kept for two weeks prior to initiating the experiment. The animal was fed a basal diet at libitum and housed individually in animal faoilities with oontrolled temperature (19-21° C.) and liqht (12h/12h LD). The experimental animal was prepared, anesthetized and 96 burn wound were made on the exterior two-thirds of the animal as described by Mertz et al. [*Journal Surgical Research* (1990), 48:245-248]. Burn wounds were divided into four treatment groups and evaluated at specific time intervals during a six-day period. Burn wounds were assigned to one of the following treatment groups: (1) Vibriolysin in Silvadene TM cream (Marion) (1,200 units per g), (2) Travase ointment (1,200 units per g), (3) Silvadene cream control, (4) no treatment control. All treatment groups were covered with Tegaderm TM polyurethane dressing which is gas permeable, clear and provides a barrier to external microbial attack. Treatments were immediate or delayed in order to assess prevention of eschar formation and debridement of hardened eschars (96 hours post-burn), respectively.

For the control groups of this experiment, burn wounds that did not receive any treatment formed relatively hard eschars after four days whereas Silvadene cream treatment of burn wounds resulted in slightly softer eschar.

Travase ointment treatment of burn wounds treated on days 1, 2, and 3 developed a concave configuration which was evident upon palpation. In addition, erythema was noted around the wounds throughout the 6-day treatment period. These results suggest that Travase treatment increased the depth of necrosis and was irritating the surrounding skin. These observations are consistent with those of Zawacki [*Surgery* (1974) 77:132] who showed that Travase not only destroyed marginally viable cells but 10 actually deepened the level of injury in a second-degree burn. Eschars of burns treated on the latter days of the experiment (after eschar development) did begin to soften and dissolve necrotic tissue within 24 hours of treatment. However, erythema was noted.

Vibriolysin prevented significant eschar formation of burn wounds receiving treatment immediately after wounding. Unlike Travase treatment, which resulted in a deepening of the wounds, vibriolysin ointment did not hydrolyze viable tissue components. Most significantly, vibriolysin treated wounds exhibited wound contracture as indicated by smaller eschar size. Treatment of burns on days 4, 5, and 6 (after eschar development) caused the eschars to soften and dissolve within 24 hours, as evidenced by softening of wound surfaces, the volume of fluid generated, and the absence of fibrin crust formation. A light erythema was noted for only one treatment period —4 days post burn. Thus, the enzyme of the invention, unlike other such enzyme products, is an effective debriding agent that encourages wound healing.

We claim:

1. A composition comprising at least one pharmaceutically acceptable carrier admixed with a protease in an effective amount for treating wounds, said protease selected from the group consisting of:
   (a) an extracellular neutral protease produced by cultivation of *Vibrio proteolyticus* ATCC 53559, said protease characterized by the following properties:
      i. hydrolyzes components of necrotic tissue including denatured collagen, elastin, and fibrin;
      ii. does not substantially hydrolyze native tissue in vivo; and
      iii. exhibits about 80% to about 95% activity when stored at 25° C. in a topical formulation for at least sixty days; and
   (b) a protease expressed by recombinant host cells which have been transformed or transfected with an expression vector for said protease (a).

2. The composition of claim 1 which is useful for debriding wounds.

3. The composition of claim 1 which is useful for promoting wound healing.

4. The composition of claim 1 wherein said protease is encoded by a DNA sequence as illustrated in FIG. 1.

5. The composition of claim 1 which is suitable for topical administration.

6. The composition of claim 1 wherein said carrier is hydrophobic.

7. The composition of claim 1 wherein said carrier is hydrophilic.

8. The composition of claim 1 which further comprises antibiotics.

9. The composition of claim 3 wherein the protease is further characterized by the ability to effect wound contracture.

10. A method of debriding wounds comprising administering to a wound an effective amount for debriding wounds of the composition of claim 1.

11. The method of claim 10 wherein said wound is a burn.

12. A method for healing wounds comprising administering to a wound an effective amount for healing wounds of the composition of claim 1.

13. The method of claim 12 wherein said wound is a burn.

14. A method of removing necrotic tissue from a wound comprising contacting said wound with an effective amount for removing necrotic tissue of a protease selected from the group consisting of:
   (a) an extracellular neutral protease produced by cultivation of *Vibrio proteolyticus* ATCC 53559, said protease characterized by the following properties:
      i. hydrolyzes components of necrotic tissue including denatured collagen, elastin, and fibrin;
      ii. does not substantially hydrolyze native tissue in vivo; and iii. exhibits about 80% to about 95% activity when stored at 25° C. in a topical formulation for at least sixty days; and
(b) a protease expressed by recombinant host cells which have been transformed or transfected with an expression vector for said protease (a).

15. The method of claim 14 wherein said wound is a burn.

16. The method of claim 14 wherein said protease is encoded by a DNA sequence as illustrated in FIG. 1.

17. The method of claim 14 wherein said protease is admixed with at lest one pharmaceutically acceptable carrier prior to being administered.

18. The method of claim 14 wherein said protease is applied topically to the wound.

19. A method for enhancing wound healing comprising administering to a wound a therapeutically effective amount for enhancing wound healing of a protease selected from the group consisting of:
(a) an extracellular neutral protease produced by cultivation of *Vibrio proteolyticus* ATCC 53559, said protease characterized by the following properties:
i. hydrolyzes components of necrotic tissue including denatured collagen, elastin, and fibrin;
ii. does not substantially hydrolyze native tissue in vivo; and
iii. exhibits about 80% to about 95% activity when stored at 25° C. in a topical formulation for at least sixty days; and
(b) a protease expressed by recombinant host cells which have been transformed or transfected with an expression vector for said protease (a).

20. The method of claim 19 wherein said wound is a burn.

21. The method of claim 19 wherein said protease is encoded by a DNA sequence as illustrated in FIG. 1.

22. The method of claim 19 wherein said protease is admixed with at least one pharmaceutically acceptable carrier prior to being administered.

23. The method of claim 19 wherein said protease is applied topically to the wound.

24. A method for hydrolyzing burn eschar comprising administering to burned tissue a therapeutically effective amount hydrolyzing burn eschar of a protease selected from the group consisting of:
(a) an extracellular neutral protease produced by cultivation of *Vibrio proteolyticus* ATCC 53559, said protease characterized by the following properties:
i. hydrolyzes components of necrotic tissue including denatured collagen, elastin, and fibrin;
ii. does not substantially hydrolyze native tissue in vivo; and
iii. exhibits about 80% to about 95% activity when stored at 25° C. in a topical formulation for at least sixty days; and
(b) a protease expressed by recombinant host cells which have been transformed or transfected with an expression vector for said protease (a).

25. The method of claim 24 wherein said protease is encoded by a DNA sequence as illustrated in FIG. 1.

26. The method of claim 24 wherein said protease is admixed with at least one pharmaceutically acceptable carrier prior to being administered.

27. The method of claim 24 wherein said protease is applied topically to the burned tissue.

* * * * *